United States Patent
Jost et al.

(10) Patent No.: US 6,359,097 B1
(45) Date of Patent: Mar. 19, 2002

(54) FUNCTIONALIZED POLYORGANOSILOXANES AND ONE OF THE PROCESSES FOR THE PREPARATION THEREOF

(75) Inventors: Philippe Jost, Taluyers; Michel Peignier, Lentilly; Christian Priou, Villeurbanne, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/510,801

(22) Filed: Feb. 23, 2000

Related U.S. Application Data

(63) Continuation of application No. 08/836,592, filed as application No. PCT/FR95/01505 on Nov. 15, 1995, now abandoned.

(30) Foreign Application Priority Data

Nov. 18, 1994 (FR) ............................................. 94 14057

(51) Int. Cl.$^7$ ................................................ C08G 77/08
(52) U.S. Cl. ............................ 528/15; 528/27; 528/29; 549/215; 556/451; 556/462; 556/454
(58) Field of Search ............................... 528/27, 15, 29; 549/215; 556/451, 454, 462

(56) References Cited

U.S. PATENT DOCUMENTS 5,310,842 A * 5/1994 Ichinohe et al. ............... 528/29
5,512,640 A * 4/1996 Osawa et al. ................ 525/476

* cited by examiner

*Primary Examiner*—David W. Wu
*Assistant Examiner*—Caixia Lu

(57) ABSTRACT

The present invention relates to multifunctionalized polyorganosiloxanes comprising, per molecule at least one functional siloxy unit Y having $C_{1-C5}$ alkoxy radical and at least one other functional siloxy unit W having an halogenated or polyhalogenated alkyl, aralkyl or aryl; polyether ether; epoxidized alkyl; alkoxyalkyl; hydroxylated, carbonylated or esterified alkyl; phenol; and alkoxysilyl; and optionally at least one siloxy unit having a SiH group. The alkoxy functionality Y is introduced onto a suitable polyhydroorganosiloxane by a dehydrogenation/condensation reaction from the alcohol from which Y derives and then the non-hydrogen functionality W by a hydrosilylation reaction from the olefinic compound from which W derives. The multifunctionalized polyorganosiloxanes can be used as antiadhesion modulators in silicone compositions.

9 Claims, No Drawings

FUNCTIONALIZED POLYORGANOSILOXANES AND ONE OF THE PROCESSES FOR THE PREPARATION THEREOF

This application is a continuation application of Ser. No. 08/836,592, filed on Aug. 20, 1997 now abandoned, which is a 371 of PCT/FR95/01505, filed on Nov. 15, 1995.

The field of the present invention is that of polyorganosiloxanes containing one or a number of functionalities introduced by substituents of the silicon and conferring specific properties on the polymers, for example antiadhesive, lubricating or compatibilizing properties and the like, which are much sought after in silicone applications.

More precisely, the present invention relates to a multifunctionalized polyorganosiloxane in which the functionalities are each carried by different siloxy units, via an SiC or SiOC bond.

The present invention also relates to a process for the functionalization of polyorganosiloxanes which makes it possible, in particular, to result in the multifunctionalized polyorganosiloxanes targeted above.

The functionalization of the polyorganosiloxanes can conventionally be carried out by substitution of the hydrogens carried by the silicon atoms of the chain.

According to a first route, this substitution can consist of a hydrosilylation reaction between a polyorganohydrosiloxane and an olefinic reagent carrying at least one $\pi$ double bond capable of reacting with the hydrogen according to an addition mechanism. Hydrosilylation is a reaction which is fully known in the technical field under consideration. This reaction is usually catalysed with platinum. It is widely described in the literature. In this respect, reference may be made, for example, to the article by V. M. Kopilov et al., Z. Obsh. Khim., vol. 57 (5), (1987) p. 1117–1127. In this first route, all the silicon atoms containing available hydrogen are substituted by organic units via SiC bonds, the said organic units being introduced by the olefinic reactant(s). One illustration, among others, of hydrosilylation is given in European Patent Application No. 504,800, which describes the addition of a polyoxyalkylene substituted by an olefinic group (vinyl) to a polydimethylhydrosiloxane of formula:

$Me_3SiO-(Me_2SiO)_{157}-(MeHSiO)_{21}-SiMe_3(Me=CH_3)$, in the presence of a monocarboxylic ester of a solvent of the alkanediol type. In this case, it clearly seems that a single type of functionalization can be envisaged and only the groups capable of being substituted by olefinic residues can be grafted onto the polyorganosiloxane.

A second functionalization route is that according to which the silicons of the polyorganosiloxane concerned are substituted by functional residues bonded to the polyorganosiloxane by virtue of SiOC bridges. The reactions which can be envisaged for doing this are, for example, those involving $\alpha,\omega$-chlorosiloxanes and alcohols or alternatively polyorganohydrosiloxanes and alcohols according to a dehydrogenation/condensation mechanism.

These dehydrogenation/condensation reactions, also described as alcoholyses of organohydropolysiloxanes, are described in particular in S. Koama and Y. Humeki, Journal of Applied Polymer Science, Vol.21 (277), pages 863–867.

This article refers to polymethylhydrosiloxanes brought into contact with an alcohol of the methanol or ethanol type and of a catalyst chosen from bases and certain metal chlorides (Lewis acids). The solvent employed is benzene. The writers thus obtain a polyalkoxymethylsiloxane which itself also has only one functionality.

Record has also been had to dehydrogenation/condensation in the invention described by U.S. Pat. No. 5,310,842 relating to alkoxy-substituted polyorganosiloxanes. These products comprise dimethylsiloxy and methylalkoxysiloxy units and contain from 4 to 30 carbon atoms. The catalyst employed in this dehydrogenation/condensation is platinum-containing in nature (chloroplatinic acid). All the starting methylhydrosiloxy functionalities are converted (degree of conversion greater 99%) to alkoxy-substituted units. The alkoxylated side chains are involved in the compatibilization of the polyorganosiloxanes with other products such as, for example, organic polymers, with which they are used in the final applications. Although the writers maintain that these alkoxylated polyorganosiloxanes have good resistance to hydrolysis, it may be permitted to doubt this, taking into account the not insignificant sensitivity of the oxygen bridge in this respect. In addition, this prior invention retains the disadvantage of the monofunctionalization of the polyorganosiloxane.

This review of the prior art makes it appear that multifunctionalized polyorganosiloxanes are lacking. Such products would nevertheless be highly appreciable in certain uses of silicones, because it is obvious that the multifunctionalization only causes an increase in the potentialities of these products which are already very wide-ranging. The introduction of multiple functionalities by grafting would also provide the undeniable advantage of making it possible to construct silicones to measure, specifically suited to the targeted applications.

In the light of this irrefutable fact, one of the essential objects of the present invention is to provide a functionalized polyorganosiloxane, in particular a multifunctionalized polyorganosiloxane, and more particularly still a polyorganosiloxane comprising at least two siloxy sites (or units) of different functionalization, each carrying one type of functionality, corresponding to a plurality of functional types.

Another essential object of the invention is to provide a polyorganosiloxane which can be obtained simply and economically.

Another object of the present invention is to provide a monofunctionalized precursor which makes it possible to gain access to multi-, and in particular bifunctionalized, polyorganosiloxanes.

Another essential object of the invention is to provide a process for the preparation of polyorganosiloxanes having simultaneously a number of types of functional groups introduced by grafting, in particular two types of functional groups, it being necessary for the said process to be easy to implement and with a low cost price, both as regards the raw materials employed and as regards the equipment, energy and time required.

Another essential object of the invention is to provide a process for the synthesis of a precursor or of an intermediate product which makes it possible to result in the multifunctional, in particular bifunctional, polyorganosiloxanes targeted above.

In seeking to meet these objectives, the Applicant Company has discovered in an entirely surprising and unexpected way, after many studies and experiments, that, in contrast to what is taught by Koama and Humeki, the alcoholysis of polymethylhydrosiloxanes results, under certain conditions, in alkoxy-substituted siloxy units and in hydrosiloxy units in which the hydrogen has not reacted, according to a specific stoichiometry.

It follows that the present invention, which makes it possible to achieve the abovesaid objectives among others, relates, as new product per se, to a functionalized polyorganosiloxane, and more particularly a multifunctionalized polyorganosiloxane, comprising, per molecule, α—on the one hand, at least one functional siloxy unit of formula:

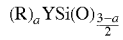          (I)

in which a=0, 1 or 2

R is a monovalent hydrocarbon radical chosen from linear or branched alkyls having from 1 to 6 atoms, in particular methyl, ethyl, propyl or butyl, and/or from aryls and in particular phenyl, methyl being more particularly preferred, the R radicals being identical or different when a=2, Y is a linear or branched alkoxy radical preferably chosen from $C_1$–$C_{15}$ alkoxys, in particular $C_1$–$C_6$ alkoxys, methoxy, ethoxy and (iso)propoxy being more particularly used, β—and, on the other hand, at least one functional siloxy unit of formula:

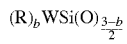          (II)

in which b=0, 1 or 2,

R corresponds to the same definition as that given above for the R substituent of the unit (I) and can be identical to or different from the latter, W is hydrogen or a monovalent hydrocarbon radical having from 2 to 30 carbon atoms and optionally S and/or O and/or halogen atoms and constituting a functional residue, bonded to the silicon via an Si—C bond, this residue preferably being chosen from the following groups:

(i) an alkyl, aralkyl or aryl group substituted by one or a number of halogen atom(s) and/or by a mono- or polyhaloalkyl radical, (2i) a polyether ether group of formula —($R^1$—O—)$_e$—$R^2$ with $R^1$ representing an alkylene group and, $R^2$ representing a hydrogen atom or an alkyl group and e=1 to 5, (3i) an epoxy group resulting from the union of an oxygen atom with two carbon atoms belonging to an alkyl, cycloalkyl or alkenyl group, (4i) an alkoxyalkyl or aryloxyalkyl group, (5i) a mono- or polyhydroxylated and/or mono- or polycarbonylated and/or mono- or polyesterified alkyl group, (6i) a sterically hindered phenol group or a group deriving from a mono- or dihydroxylated benzophenone, (7i) an alkoxysilyl, preferably trialkoxysilyl, group, γ—and, optionally, at least one siloxy unit (III) of following formula:

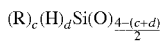          (III)

in which c=0, 1, 2 or 3, d=0 or 1 and c+d≦3, the R substituents being as defined above in the units (I) and (II).

To the knowledge of the Applicant Company, no document of the prior art describes polyorganosiloxanes having at the same time units functionalized by a functional residue bonded to the silicon via an SiOC bond and siloxy units functionalized by a functional residue bonded to the silicon via an SiC bond.

In this polyorganosiloxane according to the invention, the first alkoxy functionality Y is carried by the units of formula (I), whereas the second hydrocarbon functionality W appears in the units of formula (II) defined above.

As regards W, the specific case in which this radical corresponds to hydrogen is that illustrating the polyorganosiloxane which is the precursor of the multifunctional polyorganosiloxane and which constitutes another subject of the invention.

According to the usual terminology in silicones, these units (I) and (II) can be M, D but also T units. The presence of T units corresponds to an alternative form in which the polyorganosiloxanes exist in the form of linear chains crosslinked to one another.

The Y functional groups are characterized in that they can be hydrolysed and in that they can therefore make it possible to graft onto various substrates, which can be particularly advantageous in certain applications, e.g. antiadhesion, lubrication and the like.

W can consist of a hydrocarbon functional group which is more difficult to hydrolyse and which is capable of expressing various properties according to its chemical nature. This can be the compatibilization with organic polymers or alternatively the introduction of a crosslinking functional group into the polyorganosiloxane.

In accordance with an advantageous form of the invention, this functional substituent W is chosen from the following radicals:

a linear a alkyl radical having from 8 to 12 carbon atoms, in particular radicals with halogenated functional residues (type (i)) and of formula:

          (1)

or

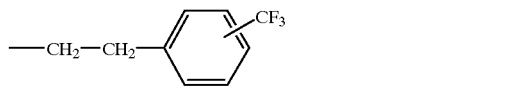          (2)

a radical with a halogenated (type (i)) and etherified (type (2i)) functional residue and of formula:

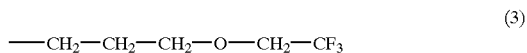          (3)

a (poly)etherified radical of type (2i) and of formula:

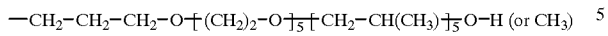   (4)

or

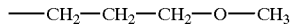   (5)

a radical of type (3i), and of formula:

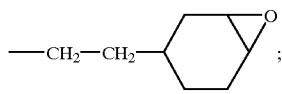   (6)

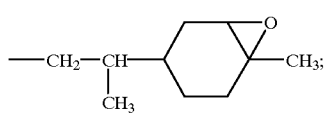   (7)

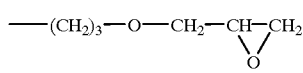   (8)

or

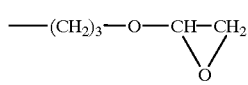   (9)

an aryloxyalkyl radical of type (4i) and of formula:

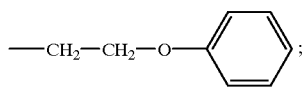   (10)

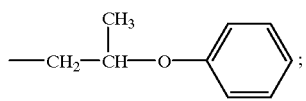   (11)

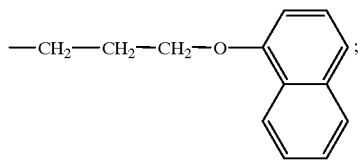   (12)

an esterified alkyl radical of type (Si) and of formula:

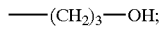   (13)

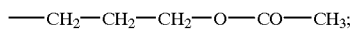   (14)

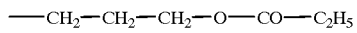   (15)

or

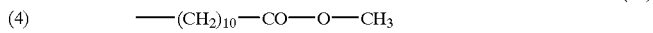   (16)

a radical of type (6i) and of formula:

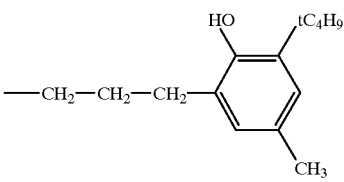   (17)

or

   (18)

a radical of type (7i) and of formula:

   (19)

or

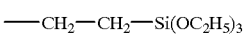   (20)

As indicated above, the invention is not limited to the case in which the polyorganosiloxane contains only two types of functionality Y and W. Indeed, according to an advantageous alternative form, the polyorganosiloxane contains, in addition to the units (I) and (II), at least one unit (III).

These SiH units (III) are, for example, residual siloxy sites in which the hydrogen has not reacted in order to be substituted by Y or W. This residual hydrogenated nature can prove to be useful in certain applications of polyorganosiloxanes according to the invention.

It should be emphasized that from the moment that a unit of a given type (I, II or III, e.g.) is present in the polyorganosiloxane in more than one form, the various forms can be identical to or different from one another.

Taking into account the values which the indices a to d attributed to the substituents in the units (I), (II), (III) can take, it should be understood that the polyorganosiloxanes according to the invention can have a linear and/or branched and/or cyclic structure.

The preferred R radicals are: methyl, ethyl, n-propyl, isopropyl or n-butyl, preferably methyl. More preferentially still, at least 80 % by number of the R radicals are methyls.

The preferred alkoxy radicals Y are the ethoxy radicals.

In order to be even more specific as regards the polyorganosiloxanes to which the invention relates, as new products, mention is first of all made of those formed by statistical, sequenced or block linear copolymers of following average formula:

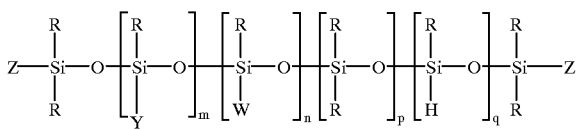

(IV)

in which:
- the symbols Y, W and R are as defined above,
- the symbol Z is a monovalent radical chosen from the radicals formed by hydrogen and from those corresponding to the definitions of R, Y and W,
- the indices m, n, p and q represent positive whole or decimal numbers and
- the sum m+n+p+q≧3, preferably between 3 and 100,
  - the scenario in which p=q=0, m≧1 and n≦50 being more particularly preferred,
  - 0≦m≦100, preferably 1≦m≦50
  - 0≦n≦100, preferably 1≦n≦50
  - 0≦p≦20, preferably 0≦p≦10
  - 0≦q≦40, preferably 0≦q≦20
  - with the conditions according to which:
    - if m=0, at least one of the Z substituents corresponds to a radical corresponding to the definition characterizing Y,
    - if n=0, at least one of the Z substituents corresponds to a radical corresponding to the definition characterizing W,
    - and if m=n=0 and p+q≧1, then one of the Z substituents corresponds to a radical corresponding to the definition characterizing Y and the other of the Z substituents corresponding to the definition characterizing W.

Mention may be made, among the more particularly preferred polyorganosiloxanes of the formula (IV), of those in which p=q=0 and 0.1≦m/n≦5, preferably 1≦m/n≦5 and more preferentially 1.5≦m/n ≦3.

An alternative to the linear structure of the polymers of formula (IV) defined above relates to the polyorganosiloxanes consisting of cyclic copolymers of following average formula:

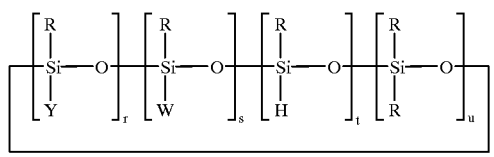

(V)

in which Y, W and R are as defined above,
and with r, s, t and u representing positive whole or decimal numbers:
- the sum r+s+t+u≧3, preferably between 3 and 8, the scenario in which t=u=0 being more particularly preferred,
- 1≦r≦8, preferably 1≦r≦4
- 1≦s≦8, preferably 1≦s≦4
- 0≦t≦8, preferably 0≦t≦4
- 0≦u≦8, preferably 0≦u≦4.

The polyorganosiloxanes according to the invention preferably consist of the products corresponding to those in which R =CH$_3$ and p=u=0 in the formulae (IV) and (V) defined above.

It is obvious that in these formulae (IV) and (V), as already indicated above, the W radicals can be identical or different in nature when n>1 and S>1.

The mixtures of polyorganosiloxanes of the type of those defined above come within the context of the present invention.

According to another of its aspects, this invention is targeted at a process for the preparation of functionalized polyorganosiloxanes, in particular multifunctionalized polyorganosiloxanes, which can in particular be those described above.

This functionalization process advantageously consists essentially in reacting
- a starting polyorganosiloxane comprising units of formula (II) as defined above, in which W represents hydrogen, with
- at least one alcohol from which the functionality Y of the unit (I) derives, and which is useful both as reactant and as reaction solvent, in the presence of a catalyst, at least one of the active elements of which is chosen from the transition metals, according to a dehydrogenation/condensation mechanism (1st stage).

One of the novel features of this process lies in the use of the alcohol corresponding to the Y group, both as reactant and as reaction solvent in this dehydrogenation/condensation stage. This is one of the essential differences from the known alcoholysis method according to Koama and Humeki. In accordance with the invention, it was possible to observe that, whatever the amount of alcohol used in the process, it is not possible to convert all the SiW functional groups with W=H of the starting polyorganosiloxane. Thus, after a certain limit degree of conversion, which varies according to the reaction conditions, the stoichiometry and the nature of the reactants, the residual SiH groups become inactive with respect to dehydrogenation/condensation. For example, in the presence of ethanol, the degree of conversion of the initial SiH functional groups levels out at 66%.

This novel dehydrogenation/condensation therefore results in a polyorganosiloxane containing at least one related functionality and free SiH functional groups. It is a precursor or an intermediate product which constitutes by itself and as such a new product per se in accordance with the invention. This precursor or this intermediate product will allow access to the multifunctional polyorganosiloxane, the preparation of which will be described in detail below.

The starting polyorganosiloxane is advantageously selected from those corresponding to the following average formula:

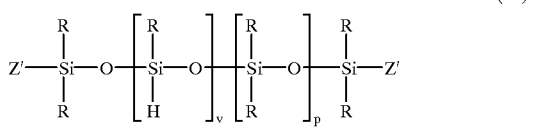

(VI)

in which:
- the R symbols are identical or different and are as defined in the legend to the formula of the units (I) and (II),
- the Z' symbols are identical or different and correspond to R or to hydrogen,
- p corresponds to the same definition as that given above in the legend to the formula (IV),
- v=m+n+q, with the condition according to which, if v=0, then p≧1 and the two Z' radicals correspond to hydrogen.

The starting polyorganohydrosiloxanes which are used, for example, in the preparation of the cyclic functionalized products are those selected from those corresponding to the following average formula:

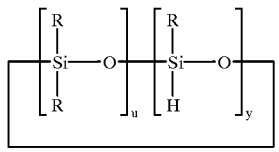

(VII)

in which:
the R symbols are identical or different and are as defined in the legend to the formula of the units (I) and (II),
u corresponds to the same definition as that given above in the legend to the formula (V),
y=r+s+t and y+u≧3.

The alcohols employed are preferably linear or branched monohydroxylated alkanols (primary, secondary or tertiary alkanols, preferably primary alkanols) preferably chosen from the following list: methanol, ethanol, (iso)propanol or (n-)butanol, ethanol being preferred.

As regards the catalyst, it is advantageously chosen from those containing at least one of the following elements: Pt, Rh, Ru, Pd, Ni and their combinations, this catalyst optionally being coupled to a support, which may or may not be inert.

According to a preferred arrangement of the invention, the catalyst is taken from the family of the platinum catalysts conventionally used for carrying out hydrosilylation reactions. These platinum catalysts are fully described in the literature. Mention may in particular be made of the complexes of platinum and of an organic product described in U.S. Pat. Nos. 3,159,601, 3,159,602, and 3,220,972 and European Patents EP-A-57,459, EP-188,978 and EP-A-190,530 and of the complexes of platinum and of vinylated organopolysiloxane described in U.S. Pat. Nos. 3,419,593, 3,715,334, 3,377,432 and 3,814,730. The Karstedt catalyst is an example of a platinum catalyst which is suitable for the process according to the invention (U.S. Pat. No. 3,775,452, Karstedt).

The nickel-based catalysts, such as for example Raney nickel, are a possible alternative to the platinum catalysts.

As regards the reaction conditions, the dehydrogenation/condensation can be carried out over a wide temperature range extending, for example, from 0 to 200° C., but it is clear that it is preferable to carry it out at a temperature between 20 and 80° C. and preferably between 40 and 70° C.

The second stage of the process according to the invention consists in preparing a multifunctionalized polyorganosiloxane from the precursor or intermediate polyorganosiloxane produced by dehydrogenation/condensation, as explained above.

To do this, the polyorganosiloxane which has been converted by dehydrogenation/condensation is reacted with at least one olefinic compound carrying at least one r bond, so as to make it possible for the converted polyorganosiloxane to add to this olefinic compound according to a hydrosilylation mechanism, in the presence of a catalyst and, preferably, at a temperature between 5 and 100° C. and more preferentially still between 20 and 90° C. This hydrosilylation therefore follows the dehydrogenation/condensation.

According to preferred methodology, the hydrosilylation is initiated by adding the olefinic compound, comprising the W radical as defined above, to the intermediate alkoxylated polyorganosiloxane, once the dehydrogenation/condensation has been completed.

In practice, this addition can take place when hydrogen evolution has ceased.

The reactive alkene can be formed by a mixture of products containing just one or a number of types of W radicals, which determine the multifunctionality of the final polyorganosiloxane.

In the case where a number of W types are provided, the alkene corresponding to the second functionality is preferably allowed to react first, then, once this alkene has completely reacted, the alkene corresponding to the third functionality is incorporated, and so on.

Instead of being added to the reaction mixture after the dehydrogenation/condensation, the olefinic compound which is the precursor of W can be used before beginning this first stage of the process, or alternatively during the latter.

According to a preferred characteristic of the invention, it is arranged for the hydrosilylation to be catalysed by at least a part of the dehydrogenation/condensation catalyst and preferably exclusively by this catalyst.

This is one of the particularly advantageous and unexpected aspects of the process of the invention. Indeed, it is entirely surprising to observe that the dehydrogenation/condensation catalyst, preferably of platinum nature, is still active in this second hydrosilylation stage.

Indeed, it is certainly known that the catalyst experiences a degree of deterioration in its performance during dehydrogenation/condensation. However, what is still more surprising is that the catalyst is present in the post-dehydrogenation/condensation medium containing polyorganosiloxanes carrying residual SiH groups. Now, in theory and according to a prejudice which is widespread in the field under consideration, the hydrosilylation catalyst, in particular a platinum catalyst, is only active if it is first brought into the presence of the reactive product comprising at least one r bond, so that the formation of an inactive colloid ought to have been observed in the case of the invention. However, none is observed.

In contrast, the residual SiH groups are particularly reactive, with respect to olefinic compounds added, by virtue of the effect of the hydrosilylation catalyst, which is itself also entirely effective. This result makes it possible to obtain, in a single sequence and without changing the reactor, a polyorganosiloxane containing a number of different functionalities.

The olefinic compounds used can be easily deduced from the definition of W given above. The choice as regards this radical is determined by the targeted applications (one or a number of different functionalities).

The hydrosilylation stage can advantageously take place at room temperature and in bulk or in solution, for example in the alcohol which was used as solvent and as reactant in the dehydrogenation/condensation reaction.

At the end of the reactions, the crude polyorganosiloxanes which are obtained can be purified, in particular by passing through a column filled with an ion exchange resin and/or by simple evaporation of the excess reactants introduced and optionally of the solvent used by heating between 100 and 180° C. under reduced pressure.

According to another of its aspects, the present invention relates to the application of the polyorganosiloxanes defined above, and of those obtained by the process which is also described above, as antiadhesion modulator and/or crosslinking agent in silicone compositions or alternatively as treatment agent for inorganic fillers, such as silica, carbonates, carbon black, and the like.

In particular, these polyorganosiloxanes can be employed as additives for surface treatment compositions, in particular for paper, concrete, metal, and the like, the said compositions advantageously being varnishes, paints, antiadhesive coatings, and the like.

Another subject of the present invention is compositions, for example silicones, comprising the polyorganosiloxanes described above as active ingredients. To be more precise, mention may be made of;

antiadhesive compositions for paper, lubricating compositions, compositions containing organic polymers and the polyorganosiloxanes under consideration provided with compatibilizing functionalities.

The present invention will be better understood in the light of the examples which follow and which describe the various multifunctionalized polyorganosiloxanes and the process for the preparation thereof. Other advantages and alternative implementational forms of the invention will also emerge from these examples.

EXAMPLES

I—1ST STAGE OF THE PROCESS ACCORDING TO THE INVENTION

Example 1

Preparation of a First Polyorganosiloxane (POS) Containing Si—OEt and Si—H Functionalities=Multifunctional POS Precursor Obtained by Dehydrogenation/condensation 200 ml of ethanol, dried beforehand over 3 angstrom molecular sieve, and 10 μl of Karstedt catalyst (10 % in hexane) are charged, under a nitrogen atmosphere, to a 500 ml, three-necked, round-bottomed flask equipped with a mechanical stirrer, a thermometer and a dropping funnel. The mixture is stirred and the dropwise addition of polymethylhydrosiloxane (40 g, $dp_n$=50) is begun. Significant hydrogen evolution is observed. The rate of addition of the Si—H fluid is adjusted in order to control the hydrogen flow and the exothermicity of the reaction. At the end of the addition, the mixture is left stirring for one hour. The excess ethanol is removed using a rotary evaporator. 59.5 g of a clear and colourless oil are recovered, with a viscosity of 52 mpa·s, corresponding to the following average formula according to an NMR analysis:

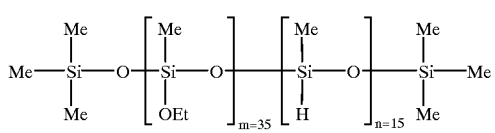

This oil exhibits very good stability on storage with moisture excluded.

Example 2

Preparation of a Second Precursor POS Containing Si—OEt and Si—H

The reactants and the procedure are the same as in Example 1. The product obtained corresponds to the same formula, apart from the difference that m=32 and n=18.

Example 3

Preparation of a Third POS Containing Si—OiPr and Si—H functionalities

The preparation is carried out as in Example 1, ethanol being replaced by isopropanol (iPr). 59.2 g of an oil are obtained, which oil corresponds to the following average formula (NMR):

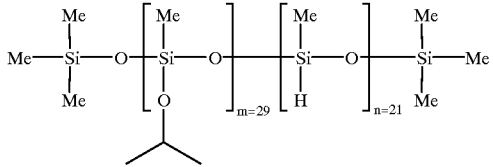

II—1 AND 2ND STAGES OF THE PROCESS ACCORDING TO THE INVENTION

Example 4

Preparation of a POS Containing Si—OEt and Si-Epoxy Functionalities

The preparation is carried out as in Example 1 but, instead of evaporating the excess alcohol, 35.3 g of vinylcyclohexene epoxide (1.5 eq/SiH) are run in dropwise. After the addition, the reaction mixture is heated at 60° C. until all the Si—H functional groups have been consumed. The excess alcohol and vinylcyclohexene epoxide are then evaporated off. 81 g of clear and slightly coloured oil are recovered. NMR analysis reveals the following structure (NMR):

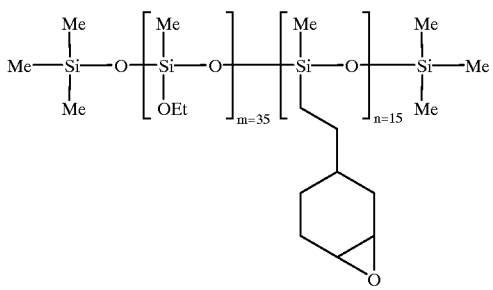

It is remarkable that, during this reaction, no opening of the epoxy functional groups by the SiH functional groups is observed.

Example 5

Preparation of Another POS Containing Si—OEt and Si-Epoxy Functionalities

The reactants and the procedure are identical to that in Example 4. The POS corresponds to the same formula, apart from the difference that m=32 and n=18.

Example 6

Preparation of a POS Containing Si—OEt and Si-methylbutylfluorohexane Functionalities The preparation is carried out as in Example 4, vinylcyclohexene oxide being replaced by the following two comonomers:

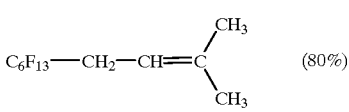

-continued

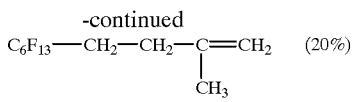

The amounts of SiOEt/SiH POS and of cbmonomers used are 25 g and 153 g respectively.

The temperature of the reaction mixture is maintained at ≅70° C.

49.09 g of SiOEt/Si-fluoroalkyl POS are recovered, which product has the formula:

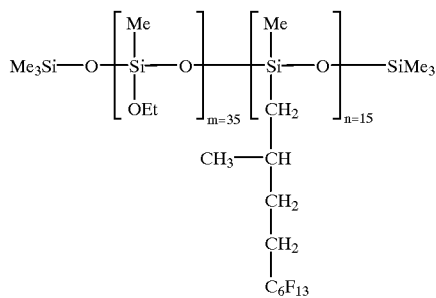

Example 7
Preparation of a POS Containing Si—OEt and Si-(methylpropyl chloride) Functionalities The preparation is carried out as in Example 4, but replacing vinylcyclohexene epoxide with methallyl chloride.

The amounts of reactants used are the following:

| | |
|---|---|
| SiOEt/SiH POS = | 100 g |
| Methallyl chloride = | 32.78 g |
| Initial Karstedt [Pt] = | 14 mg. |

The temperature of the reaction mixture is maintained at =25–30° C.

101.51 g of a clear coloured oil are recovered, which oil can be decoloured on Amberlyst H21 is resin.

NMR reveals the following formula:

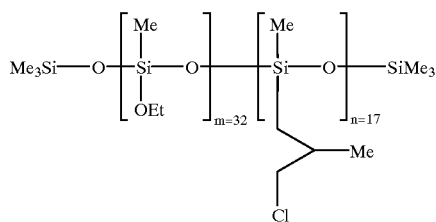

Example 8
Preparation of a POS Containing Si—OEt, Si-octyl and Si-Epoxy Functionalities

8.1. Synthesis

The preparation is carried out as in Example 4, apart from the difference that the starting material is SiOiPr/SiH POS of formula:

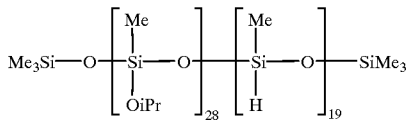

The reactants used are:

| | |
|---|---|
| +SiOiPr/SiH POS = | 78.3 g |
| +1-Octene = | 16.4 g |
| +Vinylcyclohexene epoxide (VCHE) = | 18.8 g |

Procedure:

The octene is first of all added to a POS and Karstedt [Pt] heel in isopropyl alcohol
Temperature=25°–30° C.

The reaction mixture is left until part of the SiH has been consumed (30 m).

Heating is carried out at 70° C. in order to evaporate the excess alcohol and octene.

The VCHE is added.
Temperature=25° C. This reaction temperature is maintained until consumption of SiH is complete.

Heating is again carried out at 70° C. in order to remove the excess reactant.

A clear, slightly coloured oil is recovered which has the formula:

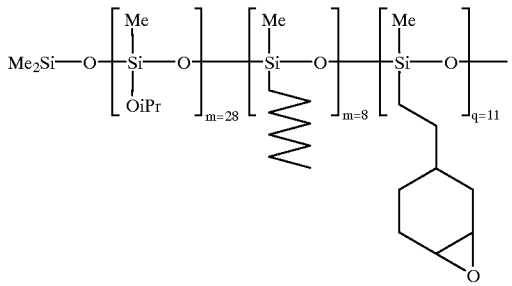

8.2. Application

The reactivity under UV of the trifunctional POS obtained is measured in the presence of 0.3% of photoinitiator consisting of a 20% by weight solution in isopropyl alcohol of ditoluyliodonium tetrakis(pentafluorophenyl)borate.

This measurement is carried out using a VNC (Vibrating needle curemeter) gel point measuring device marketed by the Company Rapra Ltd, to which a UV irradiation device has been added.

During crosslinking, the needle of the VNC, which is immersed in the mixture to be studied, will encounter a resistance which will be revealed by a decrease in the output voltage of the device. Measurements are made of the time necessary to achieve a decrease in the output voltage of the device, namely:

decrease of 10, 50 and 90% in the voltage, for a thickness to be polymerized of 2 mm.

The single figure shows the Rapra curve obtained.

The following can be read there:

| | |
|---|---|
| T10 = | 1.3 minutes |
| T80 = | 1.8 minutes |
| T95 = | 2.4 minutes |
| T100 = | 3.8 minutes |
| V10 = | 91.9 mV |
| V95 = | 12.1 mV. |

These results are entirely correct for a paper antiadhesive coating application.

Example 9

Preparation of a POS Containing Si—OEt, Si-octyl, Si-Epoxy and Si(Me)$_2$ Functionalities The reactants used are the following:

SiH/SiMe$_2$ POS of formula:

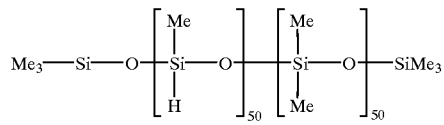

Procedure the ethanol and the Pt are charged to a 2 l, four-necked, round-bottomed flask, the POS is then run in over 2 hours, followed by the octene heating is carried out at 60° C. for 1 hour the excess VCHE is then poured in heating is carried out to 70° C., a few drops of [Pt] being added, and the reaction is maintained until consumption of the SiH groups is complete the reaction mixture is allowed to cool an oil is recovered which, on analysis by NMR, gives the following formula:

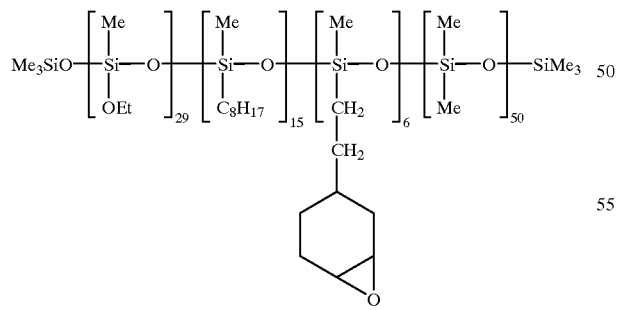

Example 10

Preparation of a POS Containing Si—OEt, Si-octyl and Si-Epoxy Functionalities

The reactants used are the following:
SiH POS of formula:

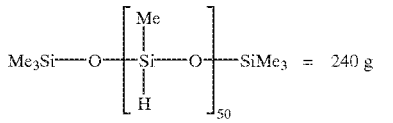

| | | |
|---|---|---|
| - EtOH | = | 1000 g |
| - [Pt] (13.6% Karstedt) | = | 35.2 mg |
| - Octene | = | 69.0 g |
| - VCHE | = | 70.0 g |

Procedure

The ethanol, the platinum and the SiH POS are charged to a 2l, three-necked, round-bottomed flask.

The temperature of the reaction mixture is initially room temperature.

The POS is slowly (3 h) introduced into the alcohol and the Pt.

During the addition, the temperature is brought to approximately 40° C. in order to be subsequently maintained at this value during the main part of the reaction.

At the end of the addition, stirring is maintained for several hours.

The octene is then gradually added. Temperature at approximately 20–40° C.

The VCHE is then finally incorporated. Temperature at approximately 40° C.

Heating is carried out at 70° C. in order to remove the excess reactants.

A clear, slightly coloured oil is recovered which, on analysis by NMR, gives the formula:

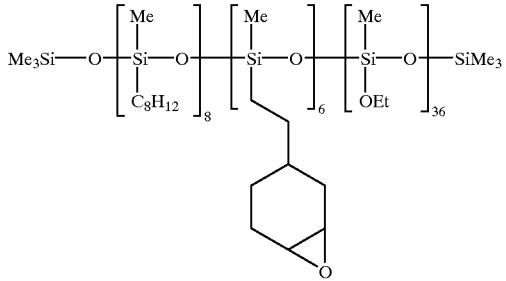

We claim:

1. A process for the preparation of a statistical, sequenced or block polyorganosiloxane of the following average formula:

(IV)

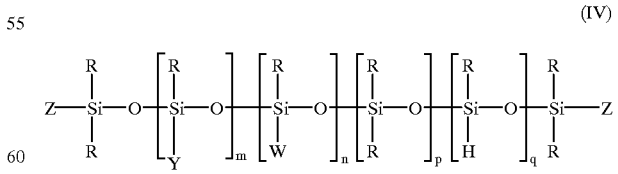

wherein:

Y is a methoxy, ethoxy, propoxy, or isopropoxy radical,

W is hydrogen or a monovalent radical having from 2 to 30 carbon atoms and optionally substituted with S, O, or halogen atoms, R are identical or different and are monovalent hydrocarbon radicals selected from the group consisting of linear alkyls having from 1 to 6 atoms, branched alkyls having from 1 to 6 atoms, and aryls, Z is R or Y, m and n, represent positive whole or decimal numbers and p and q represent 0 or positive or decimal numbers.

$100 \geq m+n+p+q \geq 3$, $1 \leq m \leq 50$, $0 \leq p \leq 10$, and $0 \leq q \leq 20$, said process comprising the steps of:

1a) reacting with an alcohol in the presence of a catalyst whose active element is a transition metal, according to a dehydrogenation/condensation mechanism, a starting polyorganosiloxane of the formula:

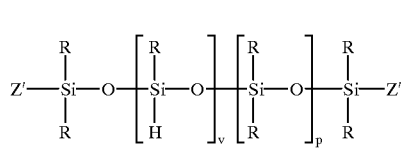
(VI)

wherein:
R are identical or different and are monovalent hydrocarbon radical selected from the group consisting of linear alkyls having from 1 to 6 atoms, branched alkyls having from 1 to 6 atoms, and aryls, Z' are identical or different and are R or hydrogen, and v=m+n+q, with the proviso that, if v=0, then $p \geq 1$ and the two Z' radicals are hydrogen; then 1b) reacting the polyorganosiloxane obtained in step 1a) with an olefinic compound carrying one π bond to carry out a hydrosilylation reaction exclusively catalysed by the catalyst used in step 1a), using step 1a) alcohol as a solvent; and 2) recovering said functionalized polyorganosiloxane.

2. A process according to claim 1, wherein R is methyl, ethyl, propyl, butyl, or phenyl; and W is selected from the group consisting of:

(i) an alkyl, a monohalogenoalkyl, a polyhalogenoalkyl, an aralkyl, a halogenoaryl, a polyhalogenoaryl, a monohalogenoalkylaryl or a polyhalogenoalkylaryl;

(2i) a polyether ether group of formula:

$$—(R^1—O—)_e—R^2$$

wherein:
$R^1$ representing an alkylene group;
$R^2$ representing a hydrogen atom or an alkyl group; and
e=1 to 5;

(3i) an epoxy group located on an alkyl, cycloalkyl or alkenyl group;

(4i) an alkoxyalkyl or aryloxyalkyl group;

(5i) a monohydroxylated alkyl, a polyhydroxylated alkyl, a monocarbonylated alkyl, a polycarbonylated alkyl, a monoesterified alkyl, or a polyesterified alkyl;

(6i) a sterically hindered phenol group or a group derived from a mono- or dihydroxylated benzophenone; and (7i) an alkoxysilyl.

3. A process according to claim 2, wherein W is selected from the group consisting of:

an optionally halogenated linear alkyl radical having from 8 to 12 carbon atoms of formula:

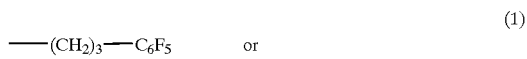
(1)

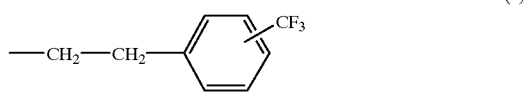
(2)

an etherified functional residue of the formula:

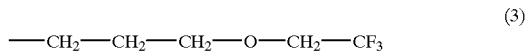
(3)

a polyetherified radical of the formula:

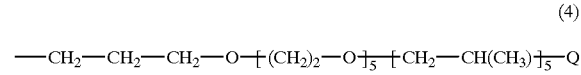
(4)

wherein Q is H or $CH_3$ or

(5)

a radical of formula:

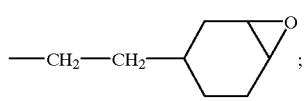
(6)

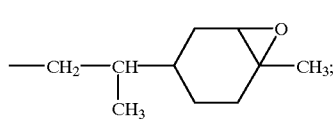
(7)

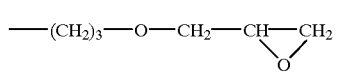
(8)

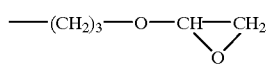
(9)

an aryloxyalkyl of formula:

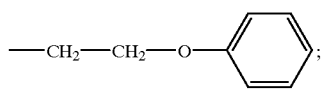
(10)

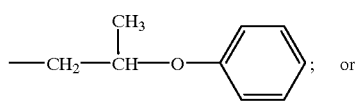
(11)

-continued (12)

—CH₂—CH₂—CH₂—O—[naphthyl];

an esterified alkyl radical of formula:

—(CH₂)₃—OH; (13)

—CH₂—CH₂—CH₂—O—CO—CH₃; (14)

—CH₂—CH₂—CH₂—O—CO—C₂H₅ (15)

or

—(CH₂)₁₀—CO—O—CH₃ (16)

a radical of formula:

(17)

—CH₂—CH₂—CH₂—[2-hydroxy-3-t-butyl-5-methylphenyl]

or (18)

—CH₂—CH₂—CH₂—[2,4-dihydroxy-3-(phenylcarbonyl)phenyl, with HO at position 4, OH at position 2, and COC₆H₅ group]

and a radical of formula:

—CH₂—Si(OCH₃)₃ (19)

or

—CH₂—CH₂—Si(OC₂H₅)₃ (20)

4. A process according to claim 1, wherein p=q=0 and $0.1 \leq m/n \leq 5$.

5. A process according to claim 1, wherein p=q=0 and R=CH₃.

6. A process according to claim 1, wherein the alcohol is methanol, ethanol, or (iso)propanol.

7. A process according to claim 1, wherein the transition metal of the catalyst is Pt, Rh, Pd, Ni, or the mixtures thereof.

8. A process according to claim 1, wherein the dehydrogenation/condensation reaction is carried out at a temperature of between 20 and 80° C.

9. A process according to claim 1, wherein the catalyst is coupled to a support.

* * * * *